(12) United States Patent
Kulmann

(10) Patent No.: US 8,076,317 B2
(45) Date of Patent: Dec. 13, 2011

(54) CONTRACEPTION PROCESS AND ADMINISTRATION FORM FOR THE SAME

(75) Inventor: Hermann Kulmann, Berlin (DE)

(73) Assignee: Bayer Pharma AG, Berlin (DE)

( * ) Notice: Subject to any disclaimer, the term of this patent is extended or adjusted under 35 U.S.C. 154(b) by 2454 days.

(21) Appl. No.: 10/380,405

(22) PCT Filed: Sep. 5, 2001

(86) PCT No.: PCT/EP01/10207
§ 371 (c)(1),
(2), (4) Date: Sep. 29, 2003

(87) PCT Pub. No.: WO02/22110
PCT Pub. Date: Mar. 21, 2002

(65) Prior Publication Data
US 2004/0219174 A1 Nov. 4, 2004

(30) Foreign Application Priority Data
Sep. 14, 2000 (DE) .................................. 100 45 380

(51) Int. Cl.
*A61K 31/56* (2006.01)
(52) U.S. Cl. ...................................................... 514/171
(58) Field of Classification Search .................. 514/170, 514/171
See application file for complete search history.

(56) References Cited

U.S. PATENT DOCUMENTS

| 5,583,129 | A | * | 12/1996 | Spona et al. .................. 514/178 |
| 5,898,032 | A | | 4/1999 | Hodgen |
| 6,225,298 | B1 | | 5/2001 | Spicer et al. |
| 6,312,722 | B1 | | 11/2001 | Schmidt-Gollwitzer et al. |

FOREIGN PATENT DOCUMENTS

| DE | 43 44 462 A4 | 6/1995 |
| DE | 195 25 017 A1 | 1/1997 |
| EP | 0 911 029 A3 | 4/1999 |
| WO | WO 96 15794 A2 | 5/1996 |
| WO | WO 9804269 A1 | 2/1998 |

OTHER PUBLICATIONS

Schwartz et al., "The trimonthly combination oral contraceptive regimen: is it cost effective?", Contraception, vol. 60, No. 5, 1999, pp. 263-267, XP002196533.
Voogd, "Postponement of Withdrawal Bleeding with a Monophasic Oral Contraceptive Containing Desogestrel and Ethinylestradiol", Contraception, Aug. 1991, vol. 44, No. 2, pp. 107-112.
Loudon et al., "Acceptability of an oral Contraceptive that Reduces the Frequency of Menstruation: The tri-cycle Pill Regiment", British Medical Journal, Aug. 20, 1977, pp. 487-490.
European Office Action corresponding to EP 01 962 996.3, dated Mar. 1, 2007.

* cited by examiner

*Primary Examiner* — San-Ming Hui
(74) *Attorney, Agent, or Firm* — Millen, White, Zelano, Branigan, P.C.

(57) ABSTRACT

Process for hormonal contraception, in which in a plurality of substantially time-unlimited, linked taking periods and optionally having a sequence lasting several years and which in each case comprise at least one taking cycle with a duration-constant taking phase lasting several days within the particular taking period and a taking pause lasting several days, in which taking phase or phases per day administration takes place of a daily unit with at least one contraceptively acting hormone component, such as estrogen and/or gestagen, and in the taking pause or pauses administration takes place either of placebos free from any hormone component or the particular taking pause remains entirely administration-free and the duration of the taking phase or phases of at least the final taking period last at least 22 days, characterized in that the duration of the taking phase or phases in any taking period proceeding a following taking period is shorter than in each case following taking period, as well as administration form for hormonal contraception and in particular for the performance thereof.

39 Claims, No Drawings

CONTRACEPTION PROCESS AND ADMINISTRATION FORM FOR THE SAME

Process for hormonal contraception, in which in a plurality of substantially time-unlimited, linked taking periods and optionally having a sequence lasting several years and which in each case comprise at least one taking cycle with a duration-constant taking phase lasting several days within the particular taking period and a taking pause lasting several days, in which taking phase or phases per day administration takes place of a daily unit with at least one contraceptively acting hormone component, such as estrogen and/or gestagen, and in the taking pause or pauses administration takes place either of placebos free from any hormone component or the particular taking pause remains entirely administration-free and the duration of the taking phase or phases of at least the final taking period lasts at least 22 days, as well as an administration form for hormonal contraception, particularly for performing the aforementioned process, with a plurality of packaging units, which in each case have at least one set of daily units to be administered within a taking cycle of a taking period, within which the duration of the taking phases is constant and comprising in each case one taking phase and a neighbouring taking pause and which in each case comprise at least one number of hormone daily units corresponding to the duration of the taking phase or phases, in each case with a content of at least one contraceptively acting hormone component, such as estrogen and/or gestagen, as well as a number of placebos corresponding to the duration of the taking pause or pauses and the duration of the taking phase or phases of at least the last of the taking periods following the first taking period amounts to at least 22 days.

Oral contraceptives are typically taken for a 21 day period. This taking phase generally follows a 7 day taking pause leading to menstruation (withdrawal bleeding). This taking regimen was developed in around 1960 because it largely corresponds to the natural cycle, but there is no medical reason for this.

Over the past 20 years tests have repeatedly been carried out with longer taking pauses demonstrating that the number of withdrawal bleedings can be reduced. In two long term studies described by N. B. Loudon et al in an article entitled "Acceptability of an oral contraceptive that reduces the frequency of menstruation: the tri-cycle pill regimen", British Medical Journal, 1977, 2, pp 487-490 or an article by A. C. Cachrimanidou et al in an article entitled "Long-interval treatment regimen with a desogestrel-containing oral contraceptive", published in Contraception 1993: 48, pp 205-216, testing took place on the one hand of a regimen involving taking for 84 days, followed by a 6 day pause and on the other taking for 63 days followed by a 7 day pause. It was established during these tests that contraceptive safety and reliability are not reduced. It was even assumed that taking errors such as e.g. forgotten tablets have a smaller influence than with conventional regimens. However, it was simultaneously established that the number of undesired vaginal spotting and breakthrough bleeding effects was increased by the extended taking phase. This also applies for short-term studies, such as e.g. that by W. S. de Voogd in an article entitled "Postponement of withdrawal bleeding with a monophasic oral contraceptive containing desogestrel and ethinylestradiol", published in Contraception 44, no. 2, August 1991, pp 107-112. The frequency of vaginal spotting and breakthrough bleeding was higher in women who had started taking oral contraceptives within the scope of the studies than in those who had taken oral contraceptives immediately beforehand. The frequency of these undesired bleeding effects was particularly high during the initial taking phase and then decreased over a period of time.

The problem of the invention is to so further develop the oral contraception process and administration form according to the preamble that the number of withdrawal bleedings is reduced whilst ensuring reliable contraception.

According to the invention this problem is solved in a further development of the aforementioned process in that the duration of the taking phase or phases is shorter than in the final taking period and that the duration of the taking phase or phases in a taking period preceding a following taking period is shorter than in the latter.

It is possible for the final taking period to commence at the latest with the tenth taking cycle.

The invention also proposes that in at least one taking period the taking phase precedes the taking pause.

It is possible that in at least one taking period the taking pause precedes the taking phase.

In the process according to the invention it is possible to proceed in such a way that the duration of at least one of the taking pauses lasts 4 to 10 days.

It is also possible for at least one of the taking pauses to last 7 days.

The invention proposes that the duration of the taking pauses remains constant as from the final taking period.

The process according to the invention can also be implemented in such a way that the duration of the talking pauses remains constant as from the first taking period.

The duration of the taking phase(s) of at least the final taking period can be at least 40 days.

It is possible to proceed in such a way that the duration of the taking phase(s) of at least the final taking period lasts at least 45 days.

The invention also proposes that the duration of the taking phase(s) of at least the final taking period lasts at least 50 days.

It is possible for the duration of the taking phase(s) of at least the final taking period to last at least 60 days.

The invention optionally provides for the duration of the taking phase(s) of at least the final taking period to last at least 70 days.

According to the invention it is possible for the duration of the taking phase(s) of at least the final taking period to last at least 80 days.

The duration of the taking phase(s) of at least the last taking period can be at least 90 days.

The invention also optionally provides for the duration of the taking phase(s) of at least the final taking period to last at least 100 days.

It is possible for the duration of the taking phase(s) of at least the final taking period to last at least 110 days.

In the process according to the invention it is also possible for the duration of the taking phase(s) of at least the final taking period to last a maximum of 150 days.

It is possible to use as the hormone component or components chlormadinone acetate with a dosage per daily unit of 0.5 to 3 mg inclusive, cyprotherone acetate 1 mg to 3 mg inclusive, desogestrel 0.05 to 0.2 mg inclusive, dienogest 1 to 3 mg inclusive, gestoden 0.035 to 0.1 mg inclusive, levonogestrel 0.025 to 0.5 mg inclusive, lynestrenol 0.25 to 3 mg inclusive, medroxyprogesterone acetate 75 to 200 mg inclusive, norethisterone 0.175 to 1.5 mg inclusive, norgestimate 0.1 to 0.3 mg inclusive, norgestrel 0.015 to 1.75 mg inclusive, norethisterone acetate 0.25 to 3 mg inclusive, norestisterone enanthate 100 to 300 mg inclusive, drosperinone 1.5 to 4 mg inclusive, ethinylestradiol 10 to 50 aeg inclusive, mestranol 25 to 50 aeg inclusive and/or estradiol (as a representative of natural estrogen) 0.25 to 6 mg inclusive.

It is finally possible to proceed in such a way that the hormone component dosage is successively decreased between taking periods.

The administration form according to the invention, particularly for performing the aforementioned process, is characterized in that the number of hormone daily units in any packaging unit corresponding to a taking period preceding the following taking period is smaller than in the packaging unit corresponding to the in each case following taking period.

It is possible for the final taking period to commence at the latest with the tenth taking cycle.

It is possible to proceed in such a way that in at least one taking period the particular taking phase precedes the particular taking pause.

The invention also proposes that in that least one taking period the particular taking pause precedes the particular taking phase.

It is possible for the number of hormone daily units per talking phase of the packaging unit corresponding to the final taking period to be at least 40.

It is also possible to proceed in such a way that the number of hormone daily units per taking phase of the packaging unit corresponding to the final taking period is at least 45.

It is possible to proceed in such a way that the number of hormone daily units per taking phase of the packaging unit corresponding to the final taking period is at least 50.

The administration form according to the invention can also be characterized in that the number of hormone daily units per taking phase of the packaging unit corresponding to the last taking period is at least 60.

It is possible for the number of hormone daily units per taking phase of the packaging unit corresponding to the final taking period to be at least 70.

The invention also proposes that the number of hormone daily units per taking phase of the packaging unit corresponding to the last taking period is at least 80.

It is possible for the number of hormone daily units per taking phase of the packaging unit corresponding to the final taking period to be at least 90.

It is also possible for the number of hormone daily units per taking phase of the packaging unit corresponding to the final taking period to be at least 100.

The invention also optionally proposes that the number of hormone daily units per taking phase of the packaging unit corresponding to the final taking period is at least 110.

The administration according to the invention can also be such that the number of hormone daily units per taking phase of the packaging unit corresponding to the final taking period is a maximum of 150.

It is also possible for the hormone daily units to in each case incorporate 0.5 to 3 mg inclusive of chlormadinone acetate, 1 to 3 mg inclusive of cyprotherone acetate, 0.05 to 0.2 mg inclusive of desogestrel, 1 to 3 mg inclusive of dienogest, 0.035 to 0.1 mg inclusive of gestoden, 0.025 to 0.5 mg inclusive of levonorgestrel, 0.25 to 3 mg inclusive of lynestrenol, 75 to 200 mg inclusive of medroxyprogesterone acetate, 0.175 to 1.5 mg inclusive of norethisterone, 0.1 to 0.3 mg inclusive or norgestimate, 0.015 to 0.75 mg inclusive of norgestrel, 0.25 to 3 mg inclusive of norethisterone acetate, 100 to 300 mg inclusive of norestisterone enanthate, 1.5 to 4 mg inclusive of drosperinone, 10 to 50 aeg inclusive of ethinylestradiol, 25 to 50 aeg inclusive of mestranol and/or 0.25 to 6 mg inclusive of estradiol (as a representative of natural estrogen).

In the administration form according to the invention it is also possible for at least one of the packaging units per taking pause to contain placebos in a number corresponding to the duration of the taking pause.

It is finally possible for the hormone component dosage to be successively reduced between taking periods.

The invention is based on the surprising finding that it is possible to solve the set problem in that the taking phases are successively extended between taking intervals.

The number of vaginal spotting and breakthrough bleeding effects occurring at the start is reduced as compared with those regimens in which as from the start the taking phase is longer than 21 or 24 days. The regimens according to the invention are particularly suitable for first users of oral contraceptives wishing to reduce the number of withdrawal bleedings.

The administration of the dosage units takes place in such a way that said dosage units are bundled as a taking cycle. If administration is e.g. to be in tablet form, then the tablets for a taking cycle can be administered with a blister. The bundle or bundles required for a taking period are offered in pack form. The packs for different taking periods are clearly marked as such. As the number of taking cycles of the final taking period is a priori unknown, the number of bundles contained is based on reasons not predetermined by the process.

It is naturally possible to use other administration forms. Thus, in the case of oral administration capsules and the like can be used in place of tablets. Transdermal administration possibilities include plasters, creams, gels, etc. It is also possible to use implants and hormone-containing IUDs, whilst in each case obviously correspondingly adapting the dosage.

The contraceptive process according to the invention for women is subdivided into at least two taking periods and with the exception of the final taking period the duration of all the periods is predetermined. The duration of the final taking period is not fixed by the process according to the invention. The taking regimen can in fact be extended at random by the user of the process according to the invention.

Each taking period consists of exactly one taking cycle or a sequence of immediately following taking cycles. A taking cycle comprises a taking phase and a taking pause, which immediately follows or immediately precedes the taking phase. During the taking phase every day use is made of a combination of e.g. an estrogen and a gestagen, a gestagen alone or another suitable substance or substance combinations. During the taking pause such a taking does not occur, but placebos can be provided. All the taking phases of the same taking periods have the same duration, which also applies to the taking pauses. The duration of the taking phases increases between the individual taking periods, but this does not necessarily apply for the taking pauses.

The invention is described in greater detail hereinafter with the aid of examples.

In the examples "E" represents a taking phase and "P" a taking pause. The directly following number indicates the duration in days. The taking periods are made apparent by underlining. The continuation dots " . . . " stand for a random repetition of the taking cycles of the final taking period. The undefined number of taking cycles of the final period is represented by the symbol "#".

EXAMPLE 1

Taking regimen: E21 P7 E42 P7 E42 P7 . . .

There are two taking periods, the number of taking cycles being 1-#. the daily hormone units contain in each case 3 mg of drospirenone and 20 aeg of ethinylestradiol.

EXAMPLE 2

Taking regimen: E21 P5 E21 P5 E49 P7 E49 P7 . . .

There are two taking periods, the number of taking cycles being 2-#. The daily hormone units in each case contain 3 mg of drospirenone and 30 aeg of ethinylestradiol.

EXAMPLE 3

Taking regimen: E24 P4 E24 P4 E24 P4 E48 P6 E48 P6 E48 P6 E48 P6 . . .

There are two taking periods and the number of taking cycles is 3-#. The daily hormone units contain in each case 0.075 mg of gestoden and 20 aeg of ethinylestradiol.

EXAMPLE 4

Taking regimen: E21 P7 E49 P7 E77 P7 E77 P7 . . .

There are three taking periods and the number of taking cycles is 1-1#. The daily hormone units in each case contain 0.075 mg of gestoden and 30 mg of ethinylestradiol.

EXAMPLE 5

Taking regimen: E20 P5 E40 P5 E40 P5 E60 P5 E60 P5 . . .

There are three taking periods and the number of taking cycles is 1-2-#. The daily hormone units contain in each case 0.15 mg of levonorgestrel and 20 aeg of ethinylestradiol.

EXAMPLE 6

Taking regimen: E30 P6 E30 P6 E30 P6 E60 P6 E60 P6 E90 P6 E90 P6 . . .

There are taking periods and the number of taking cycles is 3-2-#. The daily hormone units contain in each case 0.15 mg of levonorgestrel and 30 aeg of ethiniylestradiol.

EXAMPLE 7

Taking regimen: E21 P4 E42 P5 E63 P6 E84 P7 . . . E84 P7 . . .

There are four taking periods and the number of taking cycles is 1-1-1-#. The daily hormone units contain in each case 2 mg of cyprotherone acetate and 35 aeg of ethinylestradiol.

EXAMPLE 8

Taking regimen: E21 P7 E49 P7 E77 P7 E105 P7 E105 P7 . . .

There are four taking periods and the number of taking cycles is 1-1-1-#. The daily hormone units in each case contain 0.03 mg of norgestrel.

EXAMPLE 9

Taking regimen: E24 P4 E72 P6 E72 P6 E96 P7 E120 P7 E120 P7 . . .

There are four taking periods and the number of taking cycles is 1-2-1-#. The hormone daily units contain in each case 0.075 mg of gestoden and 20 aeg of ethinylestradiol.

EXAMPLE 10

In an administration form with E21 P7 E49 P7 E77 P7 E77 P7 . . . tablets with an estrogen/gestagen combination are administered, being supplied as packaging units in blister form and for which three different packaging units are offered.

Packaging unit 1 contains a blister with 21 tablets of the estrogen/gestagen combination, packaging unit 2 contains a blister with 49 tablets of the estrogen/gestagen combination and packaging unit 3 contains three blisters with in each case 77 tablets of the estrogen/gestagen combination.

The features disclosed in the preceding description and in the claims can be essential to the implementation of the different embodiments of the invention either singly or in random combination.

The invention claimed is:

1. A method for hormonal contraception comprising administering at least one contraceptive hormone in a plurality of linked taking periods optionally having a sequence lasting several years, wherein each of said taking periods comprises:
    at least one taking cycle, wherein each taking cycle comprises
    a duration-constant taking phase lasting several days and a taking pause lasting several days,
    wherein in each taking phase said hormonal component is administrated in a daily unit, and in each taking pause either a placebo free from any hormone component is administered or no unit is administered,
    wherein the duration of the taking phase or phases of at least the final taking period is at least 22 days, and wherein the duration of each taking phase in any taking period preceding a following taking period is shorter than that in each of the taking phases in each following taking period.

2. An administration form useful for hormonal contraception, according to a method for hormonal contraception which comprises administering at least one contraceptive hormone in a plurality of linked taking periods optionally having a sequence lasting several years, wherein each of said taking periods comprises:
    at least one taking cycle, wherein each taking cycle comprises
    a duration-constant taking phase lasting several days and a taking pause lasting several days,
    said form comprising a plurality of packaging units, each of which comprises at least one set of daily units to be administered within each of said taking cycles and wherein the duration of said taking phases is constant, said taking period in each case comprising a number of daily hormone units corresponding to the duration of each taking phase, as well as optionally a number of daily placebo units corresponding to the duration of each taking pause, the duration of the taking phase or phases of at least the last of the taking periods following the first taking period being at least 22 days, and wherein the number of daily hormone units in any packaging unit corresponding to a taking period preceding a following taking period is smaller than in the packaging unit corresponding to the in each case following taking period.

3. A method according to claim 1, wherein the final taking period starts at the latest with the tenth taking cycle.

4. A method according to claim 1, wherein in at least one taking period the taking phase precedes the taking pause.

5. A method according to claim 1, wherein in at least one taking period the taking pause precedes the taking phase.

6. A method according to claim 1, wherein the duration of at least one of the taking pauses is 4 to 10 days.

7. A method according to claim 1, wherein the duration of at least one of the taking pauses is 7 days.

8. A method according to claim 1, wherein the duration of the taking pauses in the final taking period is constant.

9. A method according to claim 1, wherein the duration of the taking pauses from and including the first taking period is constant.

10. A method according to claim 1, wherein the duration of the taking phase or phases of at least the final taking period is at least 40 days.

11. A process according to claim 10, wherein the duration of the taking phase or phases of at least the final taking period is at least 45 days.

12. A method according to claim 10, wherein the duration of the taking phase or phases of at least the final taking period is at least 50 days.

13. A method according to claim 10, wherein the duration of the taking phase or phases of at least the final taking period is at least 60 days.

14. A method according to claim 10, wherein the duration of the taking phase or phases of at least the final taking period is at least 70 days.

15. A method according to claim 10, wherein the duration of the taking phase or phases of at least the final taking period is at least 80 days.

16. A method according to claim 10, wherein the duration of the taking phase or phases of at least the final taking period is at least 90 days.

17. A method according to claim 10, wherein the duration of the taking phase or phases of at least the final taking period is at least 100 days.

18. A method according to claim 10, wherein the duration of the taking phase or phases of at least the final taking period is at least 110 days.

19. A method according to claim 10, wherein the duration of the taking phase or phases of at least the final taking period is a maximum of 150 days.

20. A method according to claim 1, wherein the hormone component or components comprises chlormadinone acetate with a dosage per daily unit of 0.5 to 3 mg inclusive, cyprotherone acetate 1 to 3 mg inclusive, desogestrel 0.05 to 0.2 mg inclusive, dienogest 1 to 3 mg inclusive, gestoden 0.035 to 0.1 mg inclusive, levonorgestrel 0.025 to 0.5 mg inclusive, lynestrenol 0.25 to 3 mg inclusive, medroxyprogesterone acetate 75 to 200 mg inclusive, norethisterone 0.175 to 1.5 mg inclusive, norgestimate 0.1 to 0.3 mg inclusive, norgestrel 0.015 to 0.75 mg inclusive, norethisterone acetate 0.25 to 3 mg inclusive, norestisterone enanthate 100 to 300 mg inclusive, drospirinone 1.5 to 4 mg inclusive, ethinylestradiol 10 to 50 µg inclusive, mestranol 25 to 50 µg inclusive and/or estradiol 0.25 to 4 mg inclusive.

21. A method Process according to claim 1, wherein the hormone component dosage is successively decreased between taking periods.

22. An administration form according to claim 2, wherein the last taking period set of daily units commences at the latest with the tenth taking cycle.

23. An administration form according to claim 2, wherein in at least one taking period the taking phase precedes the taking pause.

24. An administration form according to claim 2, wherein in at least one taking period the taking pause precedes the taking phase.

25. An administration form according to claim 2, wherein the number of daily hormone units per taking phase of the packaging unit corresponding to the last taking period is at least 40.

26. An administration form according to claim 25, wherein the number of daily hormone units per taking phase of the packaging unit corresponding to the last taking period is at least 45.

27. An administration form according to claim 25, wherein the number of daily hormone units per taking phase of the packaging unit corresponding to the last taking period is at least 50.

28. An administration form according to claim 25, wherein the number of daily hormone units per taking phase of the packaging unit corresponding to the last taking period is at least 60.

29. An administration form according to claim 25, wherein the number of daily hormone units per taking phase of the packaging unit corresponding to the last taking period is at least 70.

30. An administration form according to claim 25, wherein the number of daily hormone units per taking phase of the packaging unit corresponding to the final taking period is at least 80.

31. An administration form according to claim 25, wherein the number of daily hormone units per taking phase of the packaging unit corresponding to the last taking period is at least 90.

32. An administration form according to claim 25, wherein the number of daily hormone units per taking phase of the packaging unit corresponding to the last taking period is at least 100.

33. An administration form according to claim 25, wherein the number of daily hormone units per taking phase of the packaging unit corresponding to the last taking period is at least 110.

34. An administration form according to claim 25, wherein the number of daily hormone units per taking phase of the packaging unit corresponding to the last taking period is a maximum of 150.

35. An administration form according to claim 2, wherein the daily hormone units in each case comprise 0.5 to 3 mg inclusive of chlormadinone acetate, 1 to 3 mg inclusive of cyprotherone acetate, 0.05 to 0.2 mg inclusive of desogestrel, 1 to 3 mg inclusive of dienogest, 0.035 to 0.1 mg inclusive of gestoden, 0.025 to 0.5 mg inclusive of levonorgestrel, 0.25 to 3 mg inclusive of lynestrenol, 75 to 200 mg inclusive of medroxyprogesterone acetate, 0.175 to 1.5 mg inclusive of norethisterone, 0.1 to 0.3 mg inclusive of norgestimate, 0.015 to 0.75 mg inclusive of norgestrel, 0.25 to 3 mg inclusive of norethisterone acetate, 100 to 300 mg inclusive of norestisterone enanthate, 1.5 to 4 mg inclusive of drospirinone, 10 to 50 μg inclusive of ethinylestradiol, 25 to 50 μg inclusive of mestranol and/or 0.25 to 6 mg inclusive of estradiol.

36. An administration form according to claim 1, wherein at least one of the packaging units per taking pause has placebos in a number corresponding to the duration of the particular taking pause.

37. An administration form according to claim 2, wherein the hormone component dosage successively decreases between taking periods.

38. An administration form according to claim 2, wherein said contraceptively acting hormone component is an estrogen and/or a gestagen.

39. An administration form according to claim 2, wherein said contraceptively acting hormone component is an estrogen and/or a gestagen.

* * * * *